US010709661B2

(12) United States Patent
Guise

(10) Patent No.: US 10,709,661 B2
(45) Date of Patent: Jul. 14, 2020

(54) ORAL PARTICULATE COMPOSITION

(71) Applicant: Andrew Guise, Oxford (GB)

(72) Inventor: Andrew Guise, Oxford (GB)

( * ) Notice: Subject to any disclaimer, the term of this patent is extended or adjusted under 35 U.S.C. 154(b) by 81 days.

(21) Appl. No.: 15/916,481

(22) Filed: Mar. 9, 2018

(65) Prior Publication Data

US 2018/0263903 A1    Sep. 20, 2018

Related U.S. Application Data

(63) Continuation of application No. PCT/GB2016/052800, filed on Sep. 9, 2016.

(30) Foreign Application Priority Data

Sep. 11, 2015 (GB) ................................. 1516138.3
Jul. 6, 2016 (GB) ................................. 1611767.3

(51) Int. Cl.
| | | |
|---|---|---|
| *A61K 9/00* | (2006.01) | |
| *A61K 9/16* | (2006.01) | |
| *A61K 9/20* | (2006.01) | |
| *A61K 31/137* | (2006.01) | |
| *A61K 31/167* | (2006.01) | |
| *A61K 31/192* | (2006.01) | |
| *A61K 31/4458* | (2006.01) | |
| *A61K 31/485* | (2006.01) | |
| *A61K 31/495* | (2006.01) | |
| *A61K 31/522* | (2006.01) | |

(52) U.S. Cl.
CPC .......... *A61K 9/0056* (2013.01); *A61K 9/1623* (2013.01); *A61K 9/1635* (2013.01); *A61K 9/2081* (2013.01); *A61K 31/137* (2013.01); *A61K 31/167* (2013.01); *A61K 31/192* (2013.01); *A61K 31/4458* (2013.01); *A61K 31/485* (2013.01); *A61K 31/495* (2013.01); *A61K 31/522* (2013.01); *A61K 9/2027* (2013.01); *A61K 9/2095* (2013.01)

(58) Field of Classification Search
None
See application file for complete search history.

(56) References Cited

U.S. PATENT DOCUMENTS

| | | | |
|---|---|---|---|
| 4,263,328 A | 4/1981 | Parada et al. | |
| 5,696,095 A | 12/1997 | Piot et al. | |
| 5,711,961 A | 1/1998 | Reiner et al. | |
| 6,340,476 B1 | 1/2002 | Midha et al. | |
| 2001/0016208 A1 | 8/2001 | Valentine et al. | |
| 2003/0235613 A1 | 12/2003 | First et al. | |
| 2006/0024335 A1 | 2/2006 | Roger et al. | |
| 2008/0152763 A1 | 6/2008 | Bohannon | |
| 2009/0092672 A1 | 4/2009 | Venkatesh et al. | |
| 2013/0287856 A1* | 10/2013 | Caprasse | A61K 9/5031 424/490 |
| 2014/0010939 A1* | 1/2014 | Krohn | A23C 9/1307 426/534 |
| 2015/0044286 A1* | 2/2015 | Yoshida | A61K 31/522 424/465 |

FOREIGN PATENT DOCUMENTS

| | | |
|---|---|---|
| CA | 2 033 914 | 7/1991 |
| CA | 2 431 856 | 6/1998 |
| WO | WO 00/013523 | 3/2000 |
| WO | WO 2005/063203 | 7/2005 |
| WO | WO 2005/104712 | 11/2005 |
| WO | WO 2005/105049 | 11/2005 |
| WO | WO 2007/022317 | 2/2007 |
| WO | WO 2008/111954 | 9/2008 |
| WO | WO 2009/007770 | 1/2009 |
| WO | WO 2013/079187 | 6/2013 |
| WO | WO 2015/198067 | 12/2015 |

OTHER PUBLICATIONS

Kumar et al., "A comprehensive review on fast dissolving tablet technology," *Journal of Applied Pharmaceutical Science* 1(5):50-58, 2011.

* cited by examiner

*Primary Examiner* — Susan T Tran
(74) *Attorney, Agent, or Firm* — Klarquist Sparkman, LLP

(57) ABSTRACT

A particulate composition suitable for oral consumption comprising:

a carrier phase which is a free flowing particulate phase comprising a poor or bitter tasting agent and a first particulate agent; and a retained phase comprising a second particulate agent, wherein the second particulate agent is or comprises a flavour agent and/or a taste-masking agent, and wherein the residence time in the mouth of the retained phase ($R_{90}$: retained) is greater than the residence time in the mouth of the carrier phase ($R_{90}$: carrier).

27 Claims, No Drawings

ORAL PARTICULATE COMPOSITION

CROSS-REFERENCE TO RELATED APPLICATIONS

This application is a continuation of international application No. PCT/GB2016/052800, filed on Sep. 9, 2016, which in turn claims the benefit of Application No. GB 1516138.3, filed on Sep. 11, 2015 and Application No. GB 1611767.3, filed on Jul. 6, 2016.

These applications are incorporated herein in their entirety.

FIELD OF THE INVENTION

The invention relates to oral particulate compositions which comprise a poor-tasting or a bitter-tasting agent.

BACKGROUND

It is has been proposed to provide active agents, such as caffeine, vitamins and supplements or pharmaceutical products, in a particulate form for oral composition. Some active agents impart a poor or bitter taste when they contact the taste buds of the user.

Attempts have been made to mitigate or reduce the poor or bitter taste ordinarily imparted by a poor or bitter tasting agent when taken in the form of an oral particulate composition. These attempts include encapsulating the poor or bitter tasting agent in a non-poor or bitter tasting encapsulant, such as a lipid or carbohydrate, and/or mixing a flavour-masking agent, taste receptor blocker or taste receptor competitor with the poor or bitter tasting agent.

A known product, marketed as Firestar™, provides an oral dosage form of caffeine, a bitter tasting agent. The product comprises of a particulate composition of encapsulated caffeine particles, carrier particles of caster sugar, and flavouring. The caster sugar and flavouring function to reduce the bitter taste of the caffeine. In particular the flavouring acts to block the taste receptors and/or compete with the bitter flavour of the caffeine. The caster sugar works by reducing the amount of encapsulated caffeine particles which come into contact with taste receptors on the tongue, essentially diluting the effect of the bitter caffeine flavour, and by providing a sweet taste which competes with and/or masks the bitter taste ordinarily imparted by the caffeine particles. The sugar and the flavouring each stimulate saliva production which may lead to more rapid swallowing of the encapsulated caffeine particles, and the caster sugar and/or the flavouring may help to carry the encapsulated caffeine particles out of the mouth to be swallowed. The caster sugar and flavouring thereby reduce the residence time in the mouth of the bitter-tasting caffeine component. The caster sugar dissolves far more rapidly in the mouth than the encapsulated caffeine. These factors separately and collectively promote the sweet taste of the sugar over the bitter taste of the caffeine.

While the encapsulation, the caster sugar and the flavouring may be very effective at blocking or masking the bitter taste of the active caffeine component, the inventor in the present case has recognised that a bitter aftertaste may nonetheless reside in the mouth after the composition, comprising the encapsulated caffeine, caster sugar and flavouring, has substantially been swallowed. This may occur when the encapsulated caffeine particles are resident in the mouth long enough for the caffeine to at least partially dissolve and to contact the taste buds. This may occur when the majority of the caster sugar and flavouring has dissolved and/or been swallowed before all of the caffeine has. Retention of at least some of the encapsulated caffeine particles in the mouth longer than the other ingredients in the mouth may occur if encapsulated caffeine particles become trapped in the mouth, for example in the grooves of the tongue. The result is that a bitter or unpleasant aftertaste may persist after the bulk of the composition has been swallowed.

More generally, oral particulate compositions comprising a poor or bitter tasting active component and a carrier component (such as a sugar and/or a flavouring), in which the carrier component mitigates the effect of the bitter taste in the manner described above, may give rise to a bitter aftertaste when some of the poor or bitter tasting active component is retained in the mouth longer than the carrier component, and/or has a flavour profile which is longer-lasting than that of the carrier component. An aftertaste may also be experienced when not enough of the carrier component is provided so that the active component is not washed from the mouth sufficiently quickly to avoid release of the poor or bitter taste.

At least some of the above problems are addressed by embodiments of the invention.

SUMMARY

Previous attempts to mask the poor or bitter taste of certain ingredients have focussed on achieving rapid dissolution in the mouth and swiftly carrying away the poor tasting material.

This is evident in the pharmaceutical industry in the development of fast dissolving tablets and fast melt technology, where the critical function of the excipients is rapid dissolution and taste-masking. The present inventor, however, has found that the after taste of a poor or bitter tasting agent can be more effectively masked by formulating the poor or bitter tasting agent in a two phase formulation, where a first phase is typically a fast dissolving material, whilst the second phase is not a fast dissolving material such that it is retained in the mouth for a longer period of time.

Thus, in the present invention, a first carrier phase comprises both the poor or bitter tasting agent and a carrier component. The carrier phase is a free-flowing particulate phase which is quickly cleared from the mouth, carrying away the majority of the poor or bitter tasting agent. A second phase is referred to herein as a retained phase. This retained phase is retained in the mouth for a longer period of time than the carrier phase. The retained phase may, for example, comprise larger particles than the carrier phase, and/or may comprise a material having a lower solubility than the carrier component. The retained phase can contain a flavour agent and/or a taste-masking agent. The presence of this material in the mouth once the carrier phase has largely been cleared therefore acts to counter the bitter after-taste which can be experienced on consuming a poor or bitter tasting agent.

The present invention therefore provides a particulate composition suitable for oral consumption comprising:
  a carrier phase which is a free flowing particulate phase comprising a poor or bitter tasting agent and a first particulate agent; and
  a retained phase comprising a second particulate agent, wherein the second particulate agent is or comprises a flavour agent and/or a taste-masking agent, and wherein the second particulate agent is other than chewing gum, and wherein the residence time in the mouth of the retained phase ($R_{90}$: retained) is greater than the residence time in the mouth of the carrier phase ($R_{90}$: carrier).

Also provided is a particulate composition suitable for oral consumption comprising:

- a carrier phase which is a free flowing particulate phase comprising a poor or bitter tasting agent and a first particulate agent which is a sugar- or artificial sweetener-based carrier component; and
- a retained phase comprising a second particulate agent which is popping candy as a retained component;
- wherein the mean particle size of the sugar- or artificial sweetener-based carrier component is smaller than that of the popping candy retained component.

Also provided is a free-flowing particulate composition suitable for oral consumption, comprising:

- a carrier phase which is a free flowing particulate phase, wherein the carrier phase comprises encapsulated caffeine particles, having a mean particle size of less than 800 μm; and a sugar-based carrier component having particles with a mean particle size in the range of 100 μm to 500 μm; and
- a retained phase comprising a sugar-based retained component having particles with a mean particle size of at least 800 μm.

The invention also provides an oral dosage form of any one of the particulate compositions described herein; and well as a packaged dosage form comprising said oral dosage form.

The term poor or bitter-tasting agent as used herein generally refers to a bioactive ingredient which imparts a bitter or otherwise poor or unpleasant taste to a user.

The term particulate agent as used herein (as in first particulate agent and second particulate agent) generally refers to an ingredient having a particulate, for example a granulated or powdered form. In one aspect, the particulate agent is not poor or bitter tasting.

The term carrier component as used herein generally refers to an ingredient which provides bulk to the composition and serves to facilitate swallowing of the poor or bitter tasting agent.

The carrier component may be described herein as a first particulate agent. The term carrier phase as used herein refers to a free flowing particulate phase which comprises both the carrier component and the poor or bitter tasting agent and may additionally comprise one or more components. The carrier phase is typically made up of materials which are cleared from the mouth quickly. The components making up the carrier phase may be provided as a complex or may be bonded to one another, for example the poor or bitter tasting agent may be complexed to the carrier component. Alternatively, they may be provided as a simple mixture. The carrier phase as a whole, whether provided as a complex or a mixture, has a residence time in the mouth which is lower than that of the retained phase.

The term retained component as used herein generally refer to an ingredient which has a size and/or dissolution profile such that it is retained in the mouth longer than the carrier component/phase. The retained component may be described herein as a second particulate agent. The term retained phase as used herein refers to a phase comprising the retained component and which may comprise one or more additional components. The retained phase may comprise only (i.e. consist of) the retained component. Where the retained phase comprises more than one component, the components may be provided as a complex or they may be provided as a simple mixture. Typically, additional components in the retained phase are complexed with, bonded to or otherwise associated with the retained component such that they have a longer residence time in the mouth. The residence time in the mouth of the retained phase is higher than that of the carrier phase.

The term free flowing particulate composition as used herein generally refers to a particulate composition in which the particles generally do not stick together or coalesce to form agglomerations.

The term sugar-based as used herein generally refers to an agent consisting primarily of or comprising one or more sugars, which may be in the form of a free flowing particulate composition, typically a powder, embedded in a matrix or part of a complex, for example.

The term particle size, as used herein, may refer to mean particle size, median particle size or refer to particle size defined in terms of a particle size distribution, for example mass-median-diameter ($D_{50}$). Particle size may be determined by any appropriate measure so long as whenever a comparison is required, the same standard is applied to each agent. Suitable techniques for determining mean or median particle size, or particle size distribution are known to those skilled in the art of measuring powders and granulated materials. Examples of such techniques include the mean or median value of measurements of the longest length of particles in a sample, a mean or median value of measurements of a length measured through respective midpoints of particles in a sample, or a sieve diameter though which a predetermined portion, for example 10%, 50% or 90%, of the particles in a sample can pass. For example, a Malvern Mastersizer 3000 may used to determine mean or median particle size.

Particle size distributions can be denoted as $D_X$, where X is the mass percent of a sample which has a diameter at or below a specified size. Thus, a $D_{50}$ of 800 μm means that 50% of the mass of a sample has diameter of 800 μm or less, i.e. 50% by mass of a sample passes through a sieve having a diameter of 800 μm. The $D_{50}$ of a sample is also known as its mass-median-diameter. $D_{50}$, or other particle size distributions may also be measured using optical measuring systems. Such methods are well known to those skilled in the art. A Malvern Mastersizer 3000 may be used to determine particle size distribution.

Residence time in the mouth ($R_{90}$) as defined herein is defined as the time in which 90% of the mass of the test material is cleared from the mouth. This is determined by adding a predetermined mass of the material (e.g. 1 g) to the mouth; the contents remaining in the mouth after a set period of time (e.g. 5 seconds) is determined by emptying the contents of the mouth and measuring the mass remaining. The test is carried out without chewing. This test is then repeated at gradually increasing intervals in order to determine the time at which 90% or more of the mass has been cleared. Typically, a mean residence time is determined using results taken from at least 5 (e.g. at least 10, at least 15 or at least 20) people. When determining the residence time for the carrier phase (i.e. the phase as a whole), the test as described above is carried out on the complex, or the mixture of materials in the ratio in which they are provided within the carrier phase.

Dissolution rate in water as used herein refers to the dissolution time as determined by adding 1 g of the material to be tested to 10 ml of water at 37° C. with a magnetic stirrer rotating at 30 revs/minute. Dissolution rate is determined as the time in which 50% of the initial mass has dissolved. The mass dissolved can be determined at varying time intervals by filtration and measuring the mass remaining. Dissolution rates may be referred to herein simply as the time taken for 50% dissolution of 1 g of material, and are also referred to herein as dissolution time.

The term oral particulate composition, as used herein, means a particulate composition suitable for oral administration. Such terms may be used interchangeably.

The term popping candy, as used herein, refers to a solid composition comprising a sweetening agent and a gaseous phase. Typically the gaseous phase is present as bubbles of gas encapsulated by the solid composition. Preferably the gaseous phase is pressurised to a pressure higher than 1 atm (101 kPa). Preferably the gas comprises carbon dioxide. More preferably the gas is carbon dioxide. Typically the sweetening agent is a sugar or artificial sweetener. Examples of suitable artificial sweeteners include stevia, saccharin, aspartame, sucralose, neotame, acesulfame potassium, advantame, sorbitol, xylitol and isomalt. Particular examples of suitable artificial sweeteners include stevia, saccharin, aspartame, sucralose, neotame, acesulfame potassium, advantame, sorbitol and xylitol. Examples of suitable sugars include sucrose, glucose, fructose, galactose, mannose, ribose, xylose, maltose and lactose. Preferred sweetening agents include sucrose, dextrose, glucose, fructose, aspartame, stevia, acesulfame potassium and saccharin, e.g. sucrose, glucose (dextrose), stevia and acesulfame potassium.

DETAILED DESCRIPTION

As described herein, there is provided an oral particulate composition, typically a free flowing particulate composition suitable for oral consumption and oral administration, comprising a carrier phase and a retained phase. The carrier phase comprises a poor or bitter tasting agent and a carrier component (or first particulate agent). The retained phase comprises a retained component (second particulate agent). The retained component is, or comprises, a flavour agent and/or a taste masking agent. Thus, in one form, the composition comprises a poor or bitter tasting agent, a first particulate agent (carrier component) and a second particulate agent (retained component).

Oral particulate compositions described herein may have particular application to subpopulations in which compliance issues may be sub-optimal when using tablets, such as infants or young children (paediatric use) and certain elderly patients where, in both cases, resistance to and/or trouble taking tablets, and/or resistance to taking poor tasting powders has been noted. Specific applications may include the provision of Adderall for children and blood pressure or lipid control medications for older patients.

Clearance from the Mouth

A feature of the present invention is that the composition comprises a retained phase having flavour and/or taste-masking properties which has a greater residence time in the mouth than the carrier phase.

Thus, the residence time of the retained phase ($R_{90}$: retained) is greater than the residence time of the carrier phase ($R_{90}$: carrier), or $R_{90}$: retained > $R_{90}$: carrier. Typically, $R_{90}$: retained is at least 5 seconds greater than $R_{90}$: carrier, preferably at least 10 seconds greater, more preferably at least 15 seconds greater. For example, $R_{90}$: retained may be up to 3 minutes greater than $R_{90}$: carrier. In other words: ($R_{90}$: retained)−($R_{90}$: carrier) >0, preferably at least 5, more preferably at least 10, more preferably at least 15 seconds.

Preferred values for $R_{90}$: retained are at least 10 seconds, at least 20 seconds, at least 30 seconds or at least 1 minute, for example from 1 to 2 minutes or from 1 to 3 minutes. Preferred values for $R_{90}$: carrier are 30 seconds or less, 20 seconds or less, 10 seconds or less, most preferably 5 seconds or less or 3 seconds or less, for example from 0.5 to 20 seconds, 0.5 to 10 seconds or more preferably from 0.5 to 5 seconds or 0.5 to 3 seconds. In a preferred composition, $R_{90}$: carrier is 0.5 to 5 seconds and $R_{90}$: retained is at least 10 seconds.

Residence times in the mouth are typically reflected by dissolution rates in water under controlled conditions. Thus, a longer residence time for the retained phase can be achieved when the retained phase dissolves more slowly in water than the carrier phase. Typically, therefore, the dissolution rate of the retained phase in water, defined as set out herein, is greater than the dissolution rate in water of the carrier phase. Typically, the dissolution rate for the retained phase is at least 5 seconds, preferably at least 10 seconds, more preferably at least 15 seconds greater than the dissolution rate of the carrier phase. For example the dissolution rate of the retained phase may be up to 3 minutes, e.g. up to 1 minute or up to 30 seconds, greater than the dissolution rate of the carrier phase.

In a preferred aspect of the invention, the dissolution rate of the retained phase is at least 10 seconds but not more than 600 seconds, preferably from 20 to 500 seconds, more preferably from 30 to 300 seconds, more preferably at least one minute (e.g. 60 to 240 seconds), for example from 90 seconds to 210 seconds. Preferably, the dissolution rate of the carrier phase is 30 seconds or less, preferably 20 seconds or less, more preferably 10 seconds or less, 5 seconds or less or 3 seconds or less, e.g. from 0.5 to 20 seconds.

In a particularly preferred aspect of the invention, the carrier phase has a residence time in the mouth $R_{90}$: carrier of less than 30 seconds, e.g. from 3 to 30 seconds or from 3 to 10 seconds and the retained phase has a dissolution rate in water, determined as set out herein, of at least 30 seconds, preferably at least 45 seconds or at least one minute, e.g. from 90 seconds to 210 seconds.

The higher residence time in the mouth of the retained phase of the particulate composition may be achieved by control of a variety of parameters, in particular the particle size and solubility of the materials used. For example, a retained component may be a material which is less soluble than the carrier component and/or the poor or bitter tasting agent. In some embodiments, therefore, the retained component is a slow dissolving material or a material which will not dissolve in the mouth, for example dried fruit or fruit jelly. Nonetheless, it is preferable that the retained component is capable of fully dissolving in the mouth. It is more preferable still that the retained component is capable of fully dissolving in the mouth without chewing. This enables the full benefit of the invention to be obtained. The act of chewing before the poor or bitter tasting agent has dissolved can cause particles of the poor or bitter tasting agent to be incorporated into the retained phase, which results in the poor or bitter taste persisting in the mouth for a longer period of time. This phenomenon is particularly observed with chewing gum, where particles of the first particulate agent and the poor or bitter tasting agent can be incorporated into the chewing gum upon chewing. This results in both the poor or bitter taste persisting in the mouth and an unpleasant feeling arising from the first particulate agent grinding against a user's teeth. This problem is overcome by the use of second particulate agents which do not require chewing in order to fully dissolve in the mouth, for example second particulate agents having a residence time in the mouth of up to 3 minutes, preferably up to 2 minutes, or second particulate agents having a dissolution rate in water, as defined herein, of up to 300 seconds, up to 240 seconds or up to 210 seconds. For example, the second particulate agent is preferably not malleable.

Alternatively or additionally, the retained component may have a mean particle size which is larger than that of the poor or bitter tasting agent and/or the carrier phase, which will lead to slower dissolution. For example, the retained component may be popping candy, or particulate sugar or sweetener particles having a mean particle size of greater than 300 μm, preferably at least 500 μm or more preferably at least 800 μm. Preferably in this embodiment the particles of the carrier phase are of a smaller size, for example having a mean particle size of less than 500 μm, preferably less than 300 μm, for example less than 250 μm or less than 200 μm.

For example, the longer residence time in the mouth of the retained phase may be achieved by using a retained component which is a sugar or sweetener based particulate material having a mean particle size of at least 500 μm, preferably at least 800 μm; and a carrier phase comprising a poor or bitter tasting agent having a mean particle size of less than 500 μm, preferably less than 300 μm or less than 250 μm or less than 200 μm, and a carrier component which is a sugar or sweetener-based particulate material having a mean particle size of less than 500 μm, preferably less than 300 μm or less than 250 μm or less than 200 am.

Further particular examples of compositions which achieve the desired relative residence times in the mouth are provided below. Alternative compositions which control the residence times in the mouth in alternative ways will also provide the benefits envisaged herein, namely masking the after taste of a poor or bitter tasting agent.

Flavour

The retained phase has the effect of providing taste-masking or flavour properties which either outlast or outcompete the after taste of the poor or bitter tasting agent. Where the residence time in the mouth of the retained phase is significantly greater than that of the carrier phase, the flavour and or taste-masking effects are less important. However, where the residence time in the mouth of the retained phase is, for example, no more than 3 seconds greater than that of the carrier phase, a stronger flavour or taste-masking effect can be selected.

For example, a flavouring agent may be added to the retained component in the event that the residence time of the retained phase is no more than 3 seconds longer than that of the carrier phase. Alternatively, the retained phase may comprise particles of high intensity sugars or sweeteners such as acesulfame K, aspartame, saccharin, cyclamate and/or sucralose, which have a stronger flavour, whereas the carrier phase may comprise a sugar or sweetener with a less intense sweetness for example sucrose or fructose.

Oral Dosage Form

The carrier phase as described herein is a free flowing particulate phase. A free flowing particulate phase is made up of particles which are able to flow and therefore are not compressed, agglomerated or otherwise physically bonded to another material. The ability of the carrier phase to flow freely enables the rapid dissolution of the carrier phase on administration or consumption of the oral dosage form. Thus, the poor or bitter tasting agent is carried out of the mouth more quickly.

The retained phase is a particulate phase and may optionally be a free flowing particulate form. However, agglomerated particles also have the desired effect when present in the retained phase. The particles of the retained phase are present in the composition in a separate phase from the carrier phase. In the context of the invention, this means that the retained phase is not bonded, compressed or physically or chemically bound in any way to the particles of the carrier phase. Thus, the carrier phase and retained phase are able to move freely with respect to one another. This has the advantage that the particles maintain their differing residence times in the mouth and avoids, for example, the retained component being cleared from the mouth too quickly due to physical association with the carrier component. Compression of a mixture of retained component and carrier component into a single tablet, for example, does not lead to two separate phases within the composition which are able to move freely with respect to one another. In such tablet forms the separate ingredients are often cleared from the mouth in similar time frames due to their physical or chemical association in the tablet.

Various products described in the prior art do not achieve the advantages of the invention due to physical bonding between particles which means they do not move freely as separate phases. For example, US 2003/235613 describes a tablet comprising popping candy and other ingredients. The popping candy is either physically compressed together with the other ingredients, or all ingredients are mixed in the production of the candy, leading to a single particulate material containing all ingredients. Similarly, WO 2009/007770 describes the addition of a free-flowing agent to the surface of a chewing gum. The free flowing agent is so called because it provides free flowing properties to the particles of gum. The free flowing agent is, however, bonded or adhered to the gum particles and is therefore not itself a separate phase of free flowing particulate material. In these examples, only a single phase is present due to the physical or chemical bonding of the ingredients. The carrier phase is not provided as a separate free flowing particulate phase.

The two-phase system of the invention also has advantages over fast-melt, chewable and fast-dissolving tablets known in the art for administration of pharmaceutical products. Such products are typically provided in compressed form, e.g. as a tablet, and include mixed ingredients aimed at providing rapid dissolution. However, due to the compression of these materials into a tablet, the particles are not able to move freely in relation to one another and are not therefore present in separate phases. The present invention, which comprises a carrier phase which is a free flowing particulate phase and a separate retained phase therefore provides improved flavour and/or taste-masking properties in comparison to fast melt or fast dissolving tablets.

Description of Components of the Composition: Poor or Bitter Tasting Agent

As described herein, the poor or bitter tasting agent is a bioactive agent, or ingredient, which imparts a bitter or otherwise poor or unpleasant taste to a user. The poor or bitter taste may arise due to interaction between the poor or bitter tasting agent and type 2 taste receptors (TAS2Rs), which are known to function as bitter taste receptors. Thus, the poor or bitter tasting agent may be one which stimulates of type 2 taste receptors (TAS2Rs), in particular when placed in the mouth.

In examples, the poor or bitter tasting agent may comprise at least one of the following: caffeine; one or more vitamin or mineral or a combination thereof; and an active pharmaceutical ingredient selected from an over-the-counter drug or a prescription drug. Examples of an over-the-counter drug include an anti-inflammatory such as ibuprofen or aspirin, a painkiller (analgesic) such as paracetamol, cocodamol or codeine (e.g. paracetamol or codeine), an antihistamine, a cold or flu remedy, a health supplement, a nausea remedy, a travel-sickness remedy, a heart burn treatment, an agent to assist digestion or a combination thereof. Examples of a prescription medicine include an anti-psychotic, a cardiovascular medicine, a central nervous system medicine, a gastro-intestinal medicine, anti-infective, an anti-cancer medicine, an obesity, diabetes or pain medication including a migraine medication, a steroid, an immunological medicine, a hormonal drug, a pregnancy/IVF medication and an attention deficit hyperactivity disorder medicine, and may more particularly comprise dextromethorphan, chlorhexidine, guaifenesin, pseudoephedrine, peroxide, statins, acetaminophen, diphenhydramine, doxylamine, sildenafil citrate, loperamide, methylphenidate, amphetamine, dextroamphetamine, amphetamine/dextroamphetamine, dexmethylphenidate, lisdexamfetamine, amitriptyline, desipramine, imipramine, nortriptyline, bupropion, citalopram, escitalopram, sertraline, and venlafaxine or a combination thereof. For example, the medicine may include an anti-psychotic, a cardiovascular medicine, a central nervous system medicine, a gastro-intestinal medicine, anti-infective, an anti-cancer medicine, an obesity, diabetes or pain medication including a migraine medication, a steroid, an immunological medicine, a hormonal drug, a pregnancy/IVF medication and may particularly comprise dextromethorphan, chlorhexidine, guaifenesin, pseudoephedrine, peroxide, statins, acetaminophen, diphenhydramine, doxylamine, sildenafil citrate and loperamide or a combination thereof. It is envisaged that the invention may also have applications to non-over-the-counter drugs.

Preferred examples of medicaments for use as the poor or bitter tasting agent are (a) one or more medicaments selected from aspirin, paracetamol, ibuprofen, cocodamol and codeine, each of which may optionally be used in combination with caffeine and/or phenylephrine; (b) antihistamines; and (c) one or more medicaments selected from methylphenidate, amphetamine, dextroamphetamine, amphetamine/dextroamphetamine, dexmethylphenidate, lisdexamfetamine, methylphenidate, amitriptyline, desipramine, imipramine, nortriptyline, bupropion, citalopram, escitalopram, sertraline and venlafaxine or a combination thereof. Combinations of any of these medicaments with each other or with one or more further active agents are also envisaged. Particular examples of the poor or bitter tasting agent are (a) one or more medicaments selected from aspirin, paracetamol, ibuprofen, cocodamol and codeine, each of which may optionally be used in combination with caffeine and/or phenylephrine; and (b) antihistamines The poor or bitter-tasting agent, may, for example, comprise one or more drugs selected from acitretin, acyclovir, arecoline, buprenorphine, buserelin, buspirone, captopril, carbamazepine, carvediol, cetylpyridinium chloride, chlorhexidine diacetate, chlorpheniramine maleate, clotrimazole, cyanocobalamin, danazoi, denbufyline, diclofenac sodium, diltiazem, endomorphin 1, ergotamine tartrate, fentanyl, flurbiprofen, glucagon like peptide, gonatotropin releasing hormone, hydralazine, hydrocortisone acetate, ibuprofen, insulin, ketoprofen, lactoferrin, leu-enkephalin, lidocaine, lueinizing hormone releasing hormone, melatonin, metaclopromide, metoprolol tartrate, metronidazole, miconazole, morphine sulphate, nalbuphine, naltrexone, nicotine, nifedipine, nimesulide, nyastatin, octreotide acetate, omeprazole, oxytocin, pentazocine, pilocarpine, pindolol, piroxicam, pituitary adenylate cyclase-activating polypeptide (PACAP), prednisolone, propolis, propranolol, protrelin (TRH), recombinant human epidermal growth factor, recombinant human interferon, salcom calcitonin, silymarin, terbutaline sulphate, testosterone, theophylline, thiocolchicoside, thytropin releasing hormone, triamcinolone acetate, verapamil, methylphenidate, amphetamine, dextroamphetamine, amphetamine/dextroamphetamine, dexmethylphenidate, lisdexamfetamine, methylphenidate, amitriptyline, desipramine, imipramine, nortriptyline, bupropion, citalopram, escitalopram, sertraline and venlafaxine.

The poor or bitter-tasting agent may particularly comprise one or more drugs selected from acitretin, acyclovir, arecoline, buprenorphine, buserelin, buspirone, captopril, carbamazepine, carvediol, cetylpyridinium chloride, chlorhexidine diacetate, chlorpheniramine maleate, clotrimazole, cyanocobalamin, danazoi, denbufyline, diclofenac sodium, diltiazem, endomorphin 1, ergotamine tartrate, fentanyl, flurbiprofen, glucagon like peptide, gonatotropin releasing hormone, hydralazine, hydrocortisone acetate, ibuprofen, insulin, ketoprofen, lactoferrin, leu-enkephalin, lidocaine, lueinizing hormone releasing hormone, melatonin, metaclopromide, metoprolol tartrate, metronidazole, miconazole, morphine sulphate, nalbuphine, naltrexone, nicotine, nifedipine, nimesulide, nyastatin, octreotide acetate, omeprazole, oxytocin, pentazocine, pilocarpine, pindolol, piroxicam, pituitary adenylate cyclase-activating polypeptide (PACAP), prednisolone, propolis, propranolol, protrelin (TRH), recombinant human epidermal growth factor, recombinant human interferon, salcom calcitonin, silymarin, terbutaline sulphate, testosterone, theophylline, thiocolchicoside, thytropin releasing hormone, triamcinolone acetate and verapamil.

Pharmaceutically active ingredients present in the composition of the invention may be present in any pharmaceutically acceptable salt form. Such salt forms are well known to the skilled person. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

The poor or bitter tasting agent is provided in particulate form to assist ease of use and to increase compliance. The poor or bitter tasting agent may be a liquid absorbed into, or solution loaded onto, substrate particles. Molecules or particles of the bitter tasting agent could be covalently and/or ionically bonded with the substrate particles. Suitable substrate particles include those known in the art as carriers or excipients for pharmaceutical compositions.

In embodiments, the poor or bitter tasting agent is encapsulated. That is to say, particles of the poor or bitter tasting agent (whether provided in a ion loaded on provided in, through or with a substrate) are coated with or integrated into the structure of an encapsulating agent, or encapsulant, which is not itself poor or bitter tasting. Encapsulation helps to reduce or mitigate exposure of the taste buds to the poor or bitter tasting agent by acting as at least a partial barrier between the tongue and at least some of the poor or bitter tasting agent. Encapsulation has been found to increase the time in the mouth during which a user may comfortably hold the composition in the mouth before experiencing a poor or bitter taste. Encapsulation may also be used to control the rate of release (for example by dissolution) of the poor or bitter tasting agent. In general, the extent of encapsulation and amount of encapsulant used selected to balance the flavour-improving effects of encapsulating (in which the more the encapsulation, the better the reduction in the experience of the poor or bitter taste) against a required dissolution rate if the poor or bitter tasting agent which is needed for the bio-active effect.

The encapsulant is preferably of a material which has a slower rate of solubility in saliva than that of the first particulate agent and may have a rate of dissolution in saliva which is slower than that of the poor or bitter tasting agent. The encapsulant may itself be a material which is insoluble or barely soluble in water. In embodiments, the encapsulant may comprise one or more lipids or carbohydrates. An encapsulant may be selected to suit the properties of the poor or bitter tasting agent. In embodiments in which the poor or bitter tasting agent is caffeine, a lipid encapsulant may be used. Glyceryl Monostearate (E471) is an example of a suitable lipid. In some examples, the encapsulant may comprise at least one lipid and at least one carbohydrate, where the carbohydrate could be a sugar and/or a starch. In other examples, the encapsulant at least predominately comprises one or more carbohydrates, and preferably at least one starch which may provide a desirable rate of dissolution in saliva.

As will be appreciated, the skilled person will be familiar with various suitable encapsulation techniques, which may include one or more of a spray-drying microencapsulation technique, an air-suspension coating technique, a pan coating technique, a core-shell encapsulation technique, which may use a vibrational nozzle for example, and a centrifugal extrusion technique (if the poor or bitter tasting agent is a liquid).

Whether or not the particles are encapsulated and notwithstanding which encapsulation techniques or techniques are used, the particles of the poor or bitter tasting agent may be coated in one or more layers of sweetener, flavouring, taste masking agent or taste blocking agent, such as a sugar or candy shell.

In embodiments, the encapsulation is such that the resulting particles of encapsulated poor or bitter tasting agent comprise a core of the poor or bitter tasting agent, substantially, surrounded by a layer of encapsulant. In other examples, the resulting particles of encapsulated poor or bitter tasting agent comprise a matrix of encapsulant through which the resulting particles of encapsulated poor or bitter tasting agent is embedded and dispersed. Some particles of the poor or bitter tasting agent might protrude from the matrix. In some embodiments, a mixture of both types of encapsulated particle may be provided.

User compliance tests for caffeine particles with a lipid encapsulant have indicated that both types of encapsulation provide a significantly improved taste profile compared to non-encapsulated caffeine. Reported improvements in the taste profile include a reduced magnitude of poor or bitter taste experienced during a given residence period of the particles in the mouth and a longer residence period during which the encapsulated particles may be retained in the mouth before a significant poor or bitter taste is experienced.

The ratio of the amount of encapsulant to poor or bitter tasting agent may be selected to provide a desired particle size and/or rate of dissolution of the encapsulant and/or rate of release of the poor or bitter tasting agent. In an embodiment in which the poor or bitter tasting agent is caffeine which has been encapsulated in a lipid, e.g. Glyceryl Monostearate (E471), it has been found that a mass ratio of 1:1 encapsulant to caffeine is effective at reducing experience of a bitter taste from the caffeine.

The residence time of the poor or bitter tasting agent (whether encapsulated or not) in the mouth is typically less than 30 seconds, e.g. from 0.5 to 30 seconds, preferably from 1 to 20 seconds or from 1 to 10 seconds, most preferably from 1 to 5 seconds. Dissolution time in water (measured as defined herein) of the unencapsulated poor or bitter tasting agent is typically from 0.5 to 30 seconds, preferably from 15 to 20 seconds or from 1 to 10 seconds, most preferably from 1 to 5 seconds. Where the poor or bitter tasting agent is encapsulated, it may have a higher dissolution time in water due to the slow rate of dissolution of the encapsulant itself. Low residence times in this case may be achieved by the use of small particles (e.g. having mean particle size and/or particle distributions as set out below) and/or by combining, preferably bonding e.g. by forming a complex, of the encapsulated poor or bitter tasting agent with the first particulate agent, and/or by using a higher mass ratio of first particulate agent to poor or bitter tasting agent, which acts to carry the encapsulated poor or bitter tasting agent out of the mouth more quickly.

The size of the particles of the poor or bitter tasting agent is typically selected with reference to the size of particles in the carrier phase (which may be selected to provide bulk, good mouthfeel, and to be easily swallowed in as short a time as feasible to carry the poor or bitter tasting agent out of the mouth). The size of the particles of the poor or bitter tasting agent (whether encapsulated or not) is typically selected to be similar to, equal to, or smaller than the size of the particles of the carrier component to facilitate the action of carrier in carrying the poor or bitter tasting agent out of the mouth. Typically the size of the particles of the poor or bitter tasting agent are smaller than the size of the particles of the carrier component. This may also assist the production of packaged dosage forms of the oral particulate composition by limiting segregation during filling of containers.

Typically the particles of the poor or bitter tasting agent have a particle size distribution such that the $D_{50}$ is 800 μm or less, preferably 500 μm or less, more preferably 200 μm or less. More typically the $D_{75}$ is 800 μm or less, preferably 500 μm or less, more preferably 200 μm or less. Most typically the $D_{90}$ is 800 μm or less, preferably 500 μm or less, more preferably 200 μm or less.

Preferably, the poor or bitter tasting agent may be provided in a particulate, typically granular, form in which particles of the poor or bitter tasting agent may have a mean particle size of 800 μm or less, and/or a particle size distribution as defined above. More preferably, the poor or bitter tasting agent is provided in the form of a free-flowing particulate form, typically a powder, in which particles of the poor or bitter tasting agent may have a mean particle size of 500 μm or less, and/or a particle size distribution as defined above. Most preferably, the poor or bitter tasting agent is provided in the form of a free-flowing particulate form, typically a powder, in which particles of the poor or bitter tasting agent may have a mean particle size of 200 μm or less, and/or a particle size distribution as defined above.

In embodiments in which the poor or bitter tasting agent is encapsulated, the encapsulated poor or bitter tasting particles may have a mean particle size of 800 μm or less, and/or a particle size distribution as defined above. Preferably the encapsulated poor or bitter tasting particles may have a mean particle size of 500 μm or less, and/or a particle size distribution as defined above. More preferably the encapsulated poor or bitter tasting particles may have a mean particle size of 200 μm or less, and/or a particle size as defined above. Typically the encapsulated poor or bitter tasting agent is caffeine, and the encapsulant is a lipid. The particle size of caffeine encapsulated in a lipid is typically a mean particle size of 800 μm or less, and/or a particle size distribution as defined above, preferably a mean particle size of 500 μm or less, and/or a particle size distribution as defined above, more preferably a mean particle size of 200 μm or less, and/or a particle size as defined above.

In general, any reference to the size of particles of the poor or bitter tasting agent refers to the size of the poor or bitter tasting agent inclusive of any encapsulant which may be present.

First Particulate Agent (Carrier Component)

The first particulate agent is selected to provide at least one of the following functions: reducing the residence time of the poor or bitter tasting agent in the mouth, for example by facilitating (e.g., encouraging or increasing the speed or ease of) swallowing and/or dissolution of the poor or bitter tasting agent; reducing or mitigating the extent to which the poor or bitter tasting agent imparts a poor or bitter taste whilst in the mouth, for example by competing with, blocking or masking the flavour of the poor or bitter tasting agent; and providing bulk to increase user compliance and/or to reduce the amount of poor or bitter tasting agent that contacts the taste buds by providing at least a partial physical barrier effect.

The first particulate agent may be any agent which is capable of stimulating the production of saliva. This may facilitate, for example encourage or increase the speed or ease of, swallowing and/or dissolution of the poor or bitter tasting agent. Preferably the first particulate agent is selected to be soluble in saliva such that it dissolves in the mouth to a fluid consistency which is easily swallowed and which may facilitate swallowing of the poor or bitter tasting agent by washing or carrying the poor or bitter tasting agent out of the mouth.

Preferably the first particulate agent has a faster rate of dissolution in saliva than the poor or bitter tasting agent (whether encapsulated or not). Typically the first particulate agent has a residence time in the mouth of 20 seconds or less, preferably 10 seconds or less, more preferably 5 seconds or less for example from 0.5 to 3 seconds. The first particulate agent typically has a dissolution rate in water (as defined herein) of from 0.5 to 20 seconds, preferably up to 15 seconds, more preferably up to 10 seconds or from 1 to 5 seconds or from 1 to 3 seconds. This may provide the advantageous effect that a reduced amount of the poor or bitter tasting agent has time to dissolve in the mouth before being washed or carried out of the mouth with the dissolved or dissolving first particulate agent. In addition, when the first particulate agent is itself flavoured, selecting the solubility profile of the first particulate agent such that it dissolves in the mouth faster than the poor or bitter tasting agent may provide the advantage that the flavour of the first particulate agent is established before the poor or bitter tasting agent begins to dissolve.

In general, the first particulate agent does not impart a poor or bitter taste.

The first particulate agent may be selected to impart a flavour to mask the taste of the poor or bitter tasting agent. For example, a sweet or a salty flavour may be selected. In one example, a non-bitter citrus flavour may be selected to mask a bitter taste of a poor or bitter tasting agent to impart a citrus flavour which is more acceptable to a user than the taste of the poor or bitter tasting agent. The first particulate agent may comprise one or more constituents at least one of which may be flavoured. For example, the first particulate agent may comprise one or more sugars or artificial sweeteners, for example, a granulated sugar such as caster sugar (sucrose), optionally with an added flavouring agent. In general, the first particulate agent may comprise a substrate with an associated flavouring agent. Molecules or particles of the substrate could be bonded to, soaked in or coated in the flavour agent, which could comprise a powder, a liquid or a sugar/sweetener or candy shell, for example. One or more colourings could also be associated with the first particulate agent to improve user experience.

The first particulate agent may entrain at least some of the particles of the poor or bitter tasting agent to assist in washing or carrying the poor or bitter tasting agent out of the mouth. The first particulate agent may be selected such that it forms bonds with the poor or bitter tasting agent to assist entrainment.

The size of particles of the first particulate are selected to provide a desired dissolution time profile and/or other dissolution characteristics such as mouthfeel. Generally speaking the larger the particles, the longer they will take to dissolve. However, very small particles, i.e. powders, can dissolve so quickly that they form gels before dissolving fully. This gel can then act as one large particle. This has been found to in fact slow down the dissolution time of the full quantity of first particulate agent in a dosage form, which can lead to increased retention time of both the first particulate agent and the poor or bitter tasting agent. The optimum particle size is above the size at which at which the particles dissolve to form a gel but below the size at which they take longer than a few seconds, for example up to 5 seconds, preferably up to 3 seconds, to dissolve. In examples, a total dissolution time for the carrier phase (i.e. the first particulate agent in a dosage form comprising the first particulate agent and a poor or bitter tasting agent) of 5 seconds or less is preferred, so that substantially all of the poor or bitter tasting agent is carried out of the mouth with the dissolved first particulate agent within about 5 seconds. The optimum size distribution for optimum dissolution will vary according to the properties of the first particulate agent and the poor or bitter tasting agent used.

It has been found that the required residence and dissolution times can be achieved using first particulate agents which typically have a particle size distribution such that the $D_{50}$ is 100-800 am, preferably 100-500 μm, more preferably 200-500 μm. More typically the $D_{75}$ is 100-800 am, preferably 100-500 μm, more preferably 200-500 μm. Most typically the $D_{90}$ is 100-800 am, preferably 100-500 μm, more preferably 200-500 μm.

Sugar particles or artificial sweetener particles have been found to be particularly effective as the first particulate agent. Preferably the sugar particles or artificial sweetener particles are within the size range 100-800 μm, 100-500 μm, preferably 200-500 μm (preferably they have a mean particle size of 100-800 μm, 100-500 μm, preferably 200-500 μm) and/or have a particle size distribution as defined above. Sugar particles or artificial sweetener particles having a mean particle size of less than 100 μm, for example icing sugar which has a particle size range of about 3-110 μm with a mean particle size of about 75 μm, have been found to dissolve to form gels and are not preferred. In some embodiments, caster sugar, having a particle size range of about 150-450 μm, e.g. a mean particle size of about 300 μm is a preferred first particulate agent. Other preferred first particulate agents include acesulfame potassium, having a particle size range of about 150-450 μm, e.g. a mean particle size of about 300 μm, and sugars such as extra fine sugar (particle size range 200-600 μm, e.g. a mean particle size of about 400 μm). Sugars and artificial sweeteners have the additional benefit of conferring a sweet taste which may help with flavour masking and of providing bulk to improve user compliance and to physically inhibit at least some of the poor or bitter tasting agent from contacting the user's taste buds.

Carrier Phase

In some examples, it may be advantageous to attach, e.g., bond, particles of the poor or bitter tasting agent to particles of the first particulate agent. For example, the poor or bitter tasting agent may be provided in a complex with the first particulate agent. This may help prevent segregation during manufacturing and aid accurate filling of the end product into sachets or other containers. It may also aid entrainment of the poor or bitter tasting agent during swallowing. Respective sizes of the first particulate agent and the poor or bitter tasting agent may be selected to provide additional taste masking by producing a steric hindrance effect, i.e., wherein the first particulate agent is selected have a larger size profile than that of the poor or bitter tasting agent so that the smaller particles of the poor or bitter tasting agent are hindered from reaching and/or affecting the taste receptors whilst attached to a larger particles of the first particulate agent. In general, the first particulate agent may be selected to have a size profile relative to the poor or bitter tasting agent such as to produce a steric hindrance effect whether or not the respective particles are bonded.

The relative mass ratio of the poor or bitter tasting agent (whether encapsulated or not) to the first particulate agent is typically from 1:1 to 1:10, e.g. from 1:1 to 1:5 or about 1:3. Higher ratios (higher relative amounts of the first particulate agent) may provide greater taste-masking and may therefore be useful in the case that the poor or bitter tasting agent has a very strong flavour and/or the first particulate agent is not highly flavoured.

The carrier phase may additionally comprise one or more further components which may be provided in particulate form, or which may be bonded to, or in some way associated with, the first particulate agent and/or the poor or bitter tasting agent or encapsulate poor or bitter tasting agent. Further components which are present in the carrier phase typically have a residence time which is less than that of the poor or bitter tasting agent. Additional components include those excipients and carriers which are commonly used in fast dissolving tablet technology, for example, carriers, powdered flavours, viscosity modifiers, stabilisers, pH modifiers, taste receptor blockers and other similar materials including those described in the Journal of Applied Pharmaceutical Science 01 (05) 2011: 50-58.

Second Particulate Agent (Retained Component)

The first particulate agent is typically selected to have a residence time in the mouth which exceeds the residence time of the poor or bitter tasting agent. Since in embodiments the first particulate agent is selected to carry the poor or bitter tasting agent out of the mouth to be swallowed, the second particulate agent is typically selected to have a residence time, and typically a dissolution rate in water, which is greater than that of the first particulate agent (and thereby the poor or bitter tasting agent). Thus, the second particulate agent typically has a residence time which is greater than that of the carrier phase as a whole. Typically the second particulate agent has a residence time in the mouth of at least 10 seconds or at least 20 seconds, preferably at least 30 seconds, at least 45 seconds or at least 1 minute, for example from 1 to 3 minutes. The dissolution rate in water of the second particulate agent is typically at least 10 seconds or at least 20 seconds, more preferably at least 30 seconds, more preferably at least one minute (e.g. 60 seconds), for example from 90 seconds to 210 seconds. In general, the second particulate agent is selected to comprise particles of a larger size than particles of the first particulate agent. This may provide the effect that the second particulate agent takes longer to dissolve and remains in the mouth longer than the first particulate agent. The second particulate agent may be selected to have a solubility profile such that it dissolves more slowly in the mouth than the first particulate agent so that it lasts longer.

The second particulate agent is or comprises a flavour agent and/or a taste-masking agent. This enables the second particulate agent to either mask or compete with the bitter after taste of the poor or bitter tasting agent. Where the second particulate agent is a flavour agent, it may comprise added flavouring, or it may have a natural flavour. For example, sugars and dried fruits have a natural sweetness which acts as a flavour agent in the context of the present invention. Alternatively or additionally, the second particulate agent may comprise a particulate material having the desired residence characteristics, to which a separate flavouring agent is added, for example by bonding or complexing with the flavouring agent. Due to the residence time of the second particulate agent combined with its flavour or taste-masking properties, the second particulate agent may be selected to have a flavour profile which is longer lasting than that of the first particulate agent and more preferably longer than that of the poor or bitter tasting agent.

In general, the second particulate agent is also selected to compete with, block or mask the flavour of the poor or bitter tasting agent. This may help to mitigate or reduce a poor or bitter aftertaste which would ordinarily be imparted by any poor or bitter tasting agent residual in the mouth after dissolution and/or swallowing of the first particulate agent.

In general, the second particulate agent does not impart a poor or bitter taste.

The second particulate agent may be selected to provide a particular flavouring and/or may comprise a sweetener, flavouring or other agent to provide a desired flavour, such as a sweet or a salty flavour. The second particulate agent may have the same flavour as the first particulate agent or a different flavour. In one example, a non-bitter citrus flavour may be selected to mask a bitter taste of a poor or bitter tasting agent to impart a citrus flavour which is more acceptable to a user than the taste of the poor or bitter tasting agent. The second particulate agent may comprise one or more constituents at least one or which may be flavoured. For example, the second particulate agent may comprise popping candy or a granulated sugar, such as caster sugar (sucrose), optionally with an added flavouring agent. In general, the second particulate agent may comprise a substrate with an associated flavouring agent. Molecules or particles of the substrate could be bonded to, soaked in or coated in the flavour agent, which could comprise a powder, a liquid or a sugar/sweetener or candy shell, for example. One or more colourings could also be associated with the second particulate agent to improve user experience.

Where additional flavouring or taste-masking agents are added, these are typically bonded to or associated with the second particulate agent such that these materials are retained in the mouth along with the second particulate agent. For example, the second particulate agent may comprise compressed particles made up of sugar or sweetener and flavouring or colouring agents. The sugar/sweetener and flavour and/or colour components are compressed together into particles In general, the second particulate agent may also be selected to stimulate saliva production to increase the rate of dissolution of, and thereby reduce the residency time of, the poor or bitter tasting agent and/or the first particulate agent, including any of the poor or bitter tasting agent residual in the mouth after dissolution and/or swallowing of the first particulate agent.

The second particulate agent may be any agent which may be retained by the mouth longer than the first particulate agent and/or the poor or bitter tasting agent. The first particulate agent may be soluble, partially soluble and or insoluble in saliva. The second particulate, may dissolve and be swallowed, be chewed and be swallowed, or be chewed and removed from the mouth. Preferably it dissolves and is swallowed. Examples may include a carbonated candy such as popping candy, dried fruit or nuts, preferably popping candy. The second particulate may be sucked or chewed, preferably sucked, stimulating saliva production and releasing flavours if present. This may facilitate swallowing of any residual poor or bitter tasting agent by washing or carrying the poor or bitter tasting agent out of the mouth, and allow any flavours to compete with, block or mask that of the poor or bitter tasting agent. This may mitigate or reduce a bitter aftertaste which would ordinarily be imparted by the poor or bitter tasting agent after the bulk of the first particulate agent and poor or biter tasting agent have been dissolved or swallowed.

In general, the mass and size of the second particulate agent may be selected based on the amount of time required to remove the poor or bitter tasting agent from the mouth, for example by swallowing with the first particulate agent, and/or based on the flavour profile of the poor or bitter tasting agent. In embodiments, the more persistent the poor flavour, the greater the mass, larger and more flavoursome the second particulate is selected to be.

The second particulate agent may have the same or similar constituents or chemical composition as the first particulate agent, or the constituents or chemical composition may be different. For example, the first and second particulate agents may both substantially comprise a granulated sugar, with the first particulate agent more finely granulated than the second particulate agent. In another example, the first particulate agent may comprise a powdered sugar and the second particulate agent may comprise pieces of popping candy or dried fruit.

In general, the size of particles of the second particulate are selected to be larger than those of the first particulate agent. Typically the second particulate agent has a particle size distribution such that the $D_{50}$ is 500 µm or higher, preferably 800 µm or higher, more preferably 1000 µm or higher. More typically the $D_{75}$ is 500 µm or higher, preferably 800 µm or higher, more preferably 1000 µm or higher. Most typically the $D_{90}$ is 500 µm or higher, preferably 800 µm or higher, more preferably 1000 µm or higher.

Preferably the second particulate agent has a mean particle size of 500 µm or higher, and/or a particle size distribution as defined above. More preferably the second particulate agent has a mean particle size of 800 µm or higher, and/or a particle size distribution as defined above. Most preferably the second particulate agent has a mean particle size of 1000 µm or higher, and/or a particle size distribution as defined above. Particularly when the second particulate agent has the same or a similar chemical constitution as the first particulate agent, the larger particle size ensures that the second particulate agent dissolves more slowly in the mouth than the first particulate agent so that it is resident in the mouth longer than the first particulate agent (and the poor or bitter tasting agent). Having a larger size may also help to ensure that the second particulate agent is not entrained with the first particulate agent during swallowing of the first particulate agent and poor or bitter tasting agent. The effect is that the second particulate agent, or at least a significant portion thereof, remains resident in the mouth after dissolution and/or swallowing of the first particulate agent and poor or biter tasting agent or a majority thereof.

In general, the second particulate agent comprises particles that may be selected to have a mean particle average size which is larger than the mean particle size of the particles of the first particulate agent. Mean particle size may be determined by any appropriate measure so long as the same standard is applied to both of the first and second particulate agents. Suitable techniques for determining mean particle size may be known to those skilled in the art of measuring powders and granulated materials, and may include the mean value of measurements of the longest length of particles in a sample, a mean value of measurements of a length measured through respective midpoints of particles in a sample, or a sieve diameter though which a predetermined portion of the particles in a sample pass, for example.

The distribution of particle sizes in the second particulate agent may be such that a majority of the particles of the second particulate agent are larger than those of the first particulate agent. For example, relative size distributions may be such that 75% of the particles of the first particulate agent are larger than those of the first particulate agent, or that 90% of the particles of the first particulate agent are larger than those of the first particulate agent, for example. For example, $D_{75}$ of the second particulate agent may be greater than $D_{75}$ or $D_{90}$ of the first particulate agent. Preferably, $D_{90}$ of the second particulate agent may be greater than $D_{75}$ or $D_{90}$ of the first particulate agent.

There may be no overlap between the size of the particles of the respective first and second particulate agents, particularly in examples in which the first and second particulate agents comprises different chemical constituents.

Particularly in examples in which the first and second particulate agents comprises different chemical constituents and more particularly when the second particulate agent is less soluble per unit mass or area, than the material of the first particulate agent, for example because it comprises a material which is less soluble or because it has a less soluble coating, there may be some overlap between the upper end of the first particulate agent size distribution and the lower end of the second particulate agent size distribution without significant detriment to the technical effect of longer residency time and/or longer lasting flavour profile of the second particulate agent.

The lower end of the size distribution of the second particulate agent may be selected so that the smallest particles of the second particulate agent have a noticeably longer residency time in the mouth than the largest particles of the first particulate agent from the perspective of a user. A noticeable amount of time may be at least several seconds.

In embodiments, particles of the second particulate agent are hard and require sucking to be eaten. This may enhance saliva production and exposure of the taste buds to one or more flavours of, or associated with, the second particulate agent.

In embodiments, the second particulate is a solid or semi solid particle which may be chewed and eventually swallowed (e.g., one or more particles of a gum sweet or jelly sweet). Selecting a substantially insoluble agent will generally give rise to a longer residence time in the mouth than a solid or semi solid particle that dissolves, however, it has been noted that the act of chewing the second particulate agent can entrap residual particles of the poor or bitter tasting agent in the second particulate. In these circumstances, the second particulate may be selected to release flavours for long enough to compete with flavour of any residual poor or bitter tasting agent held in the mouth or combined with the second particulate agent as a result of chewing. Second particulate agents which do not require chewing, for example hard particles which dissolve in the mouth (e.g. on sucking) are generally preferred as this assists the free flowing of the two separate phases.

In other examples, the second particulate agent may comprise one or more particles of at least one of the following, or a combination thereof: a dried fruit, a sweet or sugar or sweetener particle, for example a gel, a jelly, a gum sweet, a mint sweet, a candy, for example a hard candy such as a boiled sweet, a soft candy or a carbonated candy such as popping candy each of which may optionally comprising one or more flavouring and/or colouring agents; for instance the second particulate agent may comprise one or more particles of at least one of the following, or a combination thereof: a dried fruit, a gel, a jelly, a gum sweet, a mint sweet, a candy, for example a hard candy such as a boiled sweet, a soft candy or a carbonated candy such as popping candy. Particles of sugar (e.g. granulated sugar), compressed powdered sweets (e.g. mints, fast dissolving sweets), hard candy (e.g. boiled sweets) and popping candy are preferred. These can be sugar-based (e.g. comprise at least 90 wt. % sugar), artificial sweetener-based (e.g. comprise at least 90 wt. % artificial sweetener), or based on a combination of artificial sweeteners and sugars (e.g. comprise at least 90 wt. % in total of artificial sweetener and sugar). Each of the particles of sugar, compressed powdered sweets, hard candy and popping candy may optionally comprise one or more flavouring and/or colouring agents. Popping candy optionally comprising one or more flavouring and/or colouring agents is particularly preferred.

Retained Phase

The retained phase is typically a single component phase, i.e. the retained phase comprises only the second particulate agent. The second particulate agent may itself comprise flavour agents, taste-masking agents and/or other additives.

The particulate composition for oral consumption or oral administration may be packed in a sachet containing sufficient particulate material for a single oral dose. The single oral dose may contain, for example, up to 3 g total composition. For example, the retained phase may be present in an amount of from 0.3 to 2.5 g, e.g. from 0.5 to 1 g, e.g. 600 mg±60 mg or 750 mg±75 mg. The carrier phase may comprise from 0.25 to 2.5 g (e.g. from 0.5 to 2 g, e.g. 1 to 2 g, e.g. 1500 mg±150 mg) of the first particulate composition and from 0.5 mg to 0.5 g, e.g. from 0.1 g to 0.5 g, e.g. 400 mg±40 mg of the poor or bitter tasting agent, for example.

Some preferred embodiments will now be described with reference to the following examples, which should be regarded in an illustrative rather than a restrictive sense.

Particular preferred examples of the compositions of the invention, wherein the poor or bitter tasting agent is a medicament, are:

Example A

Poor or bitter tasting agent comprises one or more analgesics and/or anti-inflammatory drugs which are preferably selected from aspirin, paracetamol, ibuprofen, cocodamol and codeine, each of which may optionally be used together with caffeine and/or phenylephrine (e.g. phenylephrine hydrochloride);

First particulate agent comprises caster sugar (e.g. mean particle size 150-450 μm, or about 300 μm);

Second particulate agent comprises popping candy (e.g. mean particle size 800-1500 μm, e.g. about 1 mm).

Example B

Poor or bitter tasting agent comprises one or more antihistamines;

First particulate agent comprises caster sugar (e.g. mean particle size 150-450 μm, or about 300 μm);

Second particulate agent comprises popping candy (e.g. mean particle size 800-1500 μm, e.g. about 1 mm).

Typically, in each of the above examples A and B, the total mass of composition is 2.5 g, made up of the typical dosage of the medicament, 750 mg popping candy and the remainder caster sugar. Further masking components may be used in place of some of the caster sugar if desired. For example, the composition may comprise 1-2 g, e.g. 1-1.5 g caster sugar. The medicament may be provided alone in particulate form, or it may be provided on or with an excipient, e.g. loaded onto a particulate substrate. Typically, from 0.5 mg to 500 mg of medicament is present in the composition. The compositions may be for administration to infants or children (pediatric use).

Example 1

The oral dosage form of Example 1 consisted of an oral particulate composition containing a mixture of encapsulated caffeine particles, a first particulate agent, and a second particulate agent.

The first particulate agent consisted of a mixture of caster sugar, i.e., granulated sucrose, and a commercially available powdered flavouring.

The second particulate agent consisted of popping candy, the popping candy comprising carbonated candy, flavouring and colouring. Various popping candy products may be purchased.

The caffeine was encapsulated according to techniques known in the art to provide particles comprising a matrix of a lipid-based encapsulant with caffeine particles dispersed therethough in a ratio of caffeine to encapsulant of approximately 1:1 by mass.

The oral dosage form had a total mass of 2.5 g, selected to be suitable for use by a typical adult, based on the size of the buccal cavity of a typical adult, and to provide a dosage of 180 mg of caffeine. This dosage was selected such that a typical, healthy adult might take up to two of the oral dosage forms in a day without exceeding a recommend daily intake of caffeine.

The ingredients were provided in the following amounts:

| Ingredient | Amount (%) by mass of composition | Mass (g) | Particle size range (μm) |
|---|---|---|---|
| Encapsulated caffeine (caffeine, encapsulant (glyceryl monostearate (E471)); total) | 16 | 0.18; 0.18; 0.36 | 200-500 |
| First particulate agent (caster sugar and powdered flavouring mixture) | 60 | 1.5 | 150-450 |
| Second particulate agent (popping candy) | 24 | 0.64 | 800-1500 |

User trials indicated that compliance was significantly improved by the addition of the popping candy, compared to an oral particulate composition comprising the same encapsulated caffeine and caster sugar/flavouring but excluding the second particulate agent.

The bulk of the composition, comprising the caster sugar/flavouring and encapsulated caffeine, was reported to be dissolved and swallowed in 3 to 5 seconds. The popping candy was found to continue to reside in the mouth after swallowing of the bulk of the composition, at which point users typically chewed the popping candy, which reportedly gave rise to a burst of flavour which significantly or entirely masked any poor or bitter taste of caffeine. Users reported a pleasant sensation of the bulk dissolving around the popping candy to leave the popping candy as the predominant component retained in the mouth. Users who refrained from chewing the popping candy directly following dissolution and swallowing of the bulk reported a retention time of the popping candy in the range 10 to 15 seconds and reported little to no discernible caffeine aftertaste.

In examples, the powdered flavouring could have a menthol, citric, mint, fruit or cola flavour.

Examples 2 to 6 set out other embodiments of oral particulate compositions comprising encapsulated caffeine as described in Example 1.

Example 2

The oral dosage form of Example 2 contained the same ingredients as in Example 1 in quantities selected to provide an oral dosage form having the same total size (2.5 g) as that of Example 1, in order to be suitable for consumption by an average adult, but to deliver a lower dosage of 120 mg of caffeine. This dosage was selected such that a typical, healthy adult might take up to three of the oral dosage forms in a day without exceeding a recommend daily intake of caffeine. This may provide a user an enhanced ability to modulate their caffeine intake over the course of a day.

As the mass of the encapsulated caffeine amounted to 0.24 g (compared to 0.36 g in Example 1), extra popping candy was provided to make the total mass of the composition up to the desired amount of 2.5 g. The increased amount of popping candy, both relative to the encapsulated caffeine and absolutely, was rendered the oral dosage form more like a "pure" confectionery product, and further diluted unwanted effects associated with the caffeine component.

| Ingredient | Amount (%) by mass of composition | Mass (g) | Particle size range (μm) |
|---|---|---|---|
| Encapsulated caffeine (caffeine, encapsulant; combined) | 10 | 0.12; 0.12; 0.24 | 200-500 |
| First particulate agent (caster sugar and powdered flavouring mixture) | 60 | 1.5 | 150-450 |
| Second particulate agent (popping candy) | 30 | 0.76 | 800-1500 |

Example 3

The oral dosage form of Example 3 comprised an oral particulate composition containing encapsulated caffeine as in Example 1, a first particulate agent comprising caster sugar, and a second particulate agent of particles of a hard boiled mint sweet. The second particulate agent was produced from purchased hard boiled mint sweets which were split into particles of the required size using a suitable technique. Some suitable techniques may include cutting and grinding.

The mint flavour of the second particulate agent was found to effectively mask any unwanted taste of the caffeine. The consistency of the second particulate agent was found encourage sucking, which increased saliva production, with beneficial effects on the speed of removal from the mouth of the encapsulated caffeine and enhanced flavour uptake from the second particulate agent.

| Ingredient | Amount (%) by mass of composition | Mass (g) | Particle size range (μm) |
|---|---|---|---|
| Encapsulated caffeine (caffeine, encapsulant; combined) | 14 | 0.18; 0.18; 0.36 | 200-500 |
| First particulate agent (caster sugar) | 20 | 0.5 | 150-450 |
| Second particulate agent (mint, hard boiled) | 66 | 1.64 | 800-1500 |

A variant of Example 3 in which the dosage form provides 120 mg of caffeine with an increased quantity of second particulate agent, as explained in Example 2, is also envisaged.

In other examples, the second particulate agent could be provided by particles of a compressed candy mint sweet.

Example 4

The oral dosage form of Example 4 comprised an oral particulate composition as in Example 3, but in which the second particulate agent was provided by particles of a hard boiled fruit sweet so that the retained phase provided a fruit flavour. This was found to have better compliance than the mint-flavoured composition in some users.

| Ingredient | Amount (%) by mass of composition | Mass (g) | Particle size range (μm) |
|---|---|---|---|
| Encapsulated caffeine (caffeine, encapsulant; combined) | 14 | 0.18; 0.18; 0.36 | 200-500 |
| First particulate agent (caster sugar) | 20 | 0.5 | 150-450 |
| Second particulate agent (fruit sweet - hard boiled) | 66 | 1.64 | 800-1500 |

A variant of Example 4 in which the dosage form provides 120 mg of caffeine with an increased quantity of second particulate agent, as explained in Example 2, is also envisaged.

Example 5

The oral dosage form of Example 5 comprised an oral particulate composition containing encapsulated caffeine as in Example 1, a first particulate agent of acesulfame potassium (also known as acesulfame K and Ace K), and a second particulate agent of a xylitol-based mint sweet. This provides a sugar-free alternative to the oral particulate compositions of Examples 1 to 5.

| Ingredient | Amount (%) by mass of composition | Mass (g) | Particle size range (μm) |
|---|---|---|---|
| Encapsulated caffeine (caffeine, encapsulant; combined) | 14 | 0.18; 0.18; 0.36 | 200-500 |
| First particulate agent (acesulfame K) | 20 | 0.5 | 150-450 |
| Second particulate agent (xylitol mint) | 66 | 1.64 | 800-1500 |

A variant of Example 5 in which the dosage form provides 120 mg of caffeine with an increased quantity of second particulate agent, as explained in Example 2, is also envisaged.

In other examples, the first particulate agent could be provided by aspartame or a mixture of aspartame and acesulfame K. The second particulate agent could be provided by a xylitol-based fruit sweet, when a fruit flavour is preferred to mint. In other examples, the second particulate agent could be provided by particles of xylitol and/or sorbitol, or particles of a sorbitol-based sweet.

In variations on the examples, the second particulate agent could be provided in the form of one or more larger particles of up to, for example 1.5 mm or more.

In variations of the above examples, the carrier phase could comprise a mixture of a particulate (for example granulated or powdered) sugar and one or more particulate flavourings, a particulate sugar and a particulate sweetener, or a mixture of at least two particulate sugars, such a sucrose and dextrose, optionally mixed with one or more particulate flavourings and/or colourings.

It will be appreciated that the ingredients set out in Examples 1 to 6 may be provided in different combinations.

It will be appreciated that any of Examples 1 to 6 could be adjusted to provide a different amount (for example by mass) of the poor or bitter tasting agent (active phase) by adjusting the amount of the poor or bitter tasting agent (encapsulated caffeine, in Examples 1 to 6), optionally scaling up or down the amount of the first particulate agent accordingly, and preferably adjusting the amount of the second particulate agent to make up the rest of the composition up to the required size limit of the dosage form. In general, it may be desirable to provide as much of the second particulate agent per unit amount of poor or bitter tasting agent and first particulate agent, without exceeding a comfortable dosage quantity, to increase the confectionery-like nature of the composition and reduce dilute any taste effect of the poor or bitter tasting agent. Comparative Example 6 The oral dosage form of Comparative Example 6 comprised an oral particulate composition containing encapsulated caffeine as in Example 1, a first particulate agent of caster sugar, and a second particulate agent of chewing gum.

In trials with chewing gum as the second particulate agent, it has been found that the inclination of the average user was to start chewing the mixture soon after receiving it in the mouth and before a large amount of the sugar-based first particulate agent has had time to dissolve. This was found to lead to an unpleasant tactile experience of feeling sugar particles crushing against the teeth. The act of immediately chewing the composition (rather than sucking or allowing it to temporarily rest on the tongue) was also found to slow the rate of dissolution of the first particulate agent, leading to longer retention of the caffeine component. To combat these effects, the mass of the sugar-based first particulate agent in Comparative Example 6 was reduced to the same mass as that of the encapsulated caffeine. The particle size of the first particulate agent was also reduced to improve the dissolution profile and combat the unpleasant tactile sensation. Using sugar with particle sizes in the range 100-450 μm and in a 1:1 by mass ratio with the encapsulated caffeine was found to remove the encapsulated caffeine from the mouth at a more acceptable rate.

| Ingredient | Amount (%) by mass of composition | Mass (g) | Particle size range (μm) |
|---|---|---|---|
| Encapsulated caffeine (caffeine, encapsulant; combined) | 14 | 0.18; 0.18; 0.36 | 200-500 |
| First particulate agent (caster sugar) | 20 | 0.5 | 100-450 |
| Second particulate agent (chewing gum) | 66 | 1.64 | 800-1500 |

Example 7: Sensory Test 7 members of the public were given 4 sachets of a reference composition and 3 sachets of a composition of the invention. The testers were asked to respond if any bitterness was perceived and to score the bitterness according to the following chart:
 1 No Bitterness
 2 No bitterness whilst eating, slight bitterness after product eaten
 3 Slight bitterness whilst eating that persists after eating
 4 Mild Bitterness whilst eating
 5 Unpleasant bitterness
The compositions tested were as follows:
 Ref 1: Flavour, 240 mg 50/50 encapsulated caffeine, citric acid, 2 g of fine caster sugar
 Ref 2: Flavour, 240 mg 50/50 encapsulated caffeine, 2 g of fine caster sugar
 Ref 3: Flavour, menthol, 360 mg 50/50 encapsulated caffeine, 2 g of fine caster sugar
 Ref 4: Flavour, menthol, 360 mg 50/50 encapsulated caffeine, 2 g of fine caster sugar
 Example 7.1: Flavour, 360 mg 50/50 encapsulated caffeine, citric acid, 0.75 g of fine caster sugar, 1 g flavoured popping candy
 Example 7.2: Flavour, 360 mg 50/50 encapsulated caffeine, citric acid, 0.75 g of fine caster sugar, 1 g flavoured popping candy
 Example 7.3: Flavour, 360 mg 50/50 encapsulated caffeine, citric acid, 0.75 g of fine caster sugar, 1 g flavoured popping candy Control A: 0.5 g freeze dried coffee
Control B: 0.5 g popping candy
The results are set out below:

| Example | | Respondent | | | | | | | Average Score |
|---|---|---|---|---|---|---|---|---|---|
| | | A | B | C | D | E | F | G | |
| Ref 1 | Cola | 2 | 3 | 2 | 2 | 2 | 3 | 2 | 2.29 |
| Ref 2 | Mint | 1 | 2 | 1 | 2 | 1 | 1 | 2 | 1.43 |
| Ref 3 | Cherry Max | 1 | 2 | 1 | 1 | 2 | 2 | 2 | 1.57 |
| Ref 4 | Mint Max | 1 | 2 | 2 | 1 | 2 | 1 | 2 | 1.57 |
| 7.1 | Strawberry | 1 | 2 | 1 | 1 | 1 | 1 | 1 | 1.14 |
| 7.2 | Apple & Cinnamon | 1 | 2 | 1 | 1 | 1 | 2 | 1 | 1.29 |
| 7.3 | Mint | 1 | 1 | 1 | 1 | 1 | 1 | 1 | 1 |
| Control A | | 5 | 5 | 5 | 4 | 5 | 5 | 5 | 4.86 |
| Control B | | 1 | 1 | 1 | 1 | 1 | 1 | 1 | 1 |

As can be seen from the results above, the inventive examples having a retained phase including a flavour agent provided reduced bitterness taste in a user trial, in particular a reduced after-taste.

Example 8

Examples of compositions of the invention comprising effective doses of pharmaceutical agents are given below:

| Ingredient | Amount (%) by mass of composition | Mass (g) | Particle size range (μm) |
|---|---|---|---|
| Encapsulated aspirin (aspirin, encapsulant; combined) | 24 | 0.3; 0.3; 0.6 | 200-500 |
| First particulate agent (caster sugar and powdered flavouring mixture) | 46 | 1.15 | 150-450 |
| Second particulate agent (popping candy) | 30 | 0.75 | 800-1500 |

| Ingredient | Amount (%) by mass of composition | Mass (g) | Particle size range (μm) |
|---|---|---|---|
| Encapsulated paracetamol (paracetamol, encapsulant; combined) | 30 | 0.5; 0.25; 0.75 | 200-500 |
| First particulate agent (caster sugar and powdered flavouring mixture) | 40 | 1 | 150-450 |
| Second particulate agent (popping candy) | 30 | 0.75 | 800-1500 |

| Ingredient | Amount (%) by mass of composition | Mass (g) | Particle size range (μm) |
|---|---|---|---|
| Encapsulated ibuprofen (ibuprofen, encapsulant; combined) | 16 | 0.2; 0.2; 0.4 | 200-500 |
| First particulate agent (caster sugar and powdered flavouring mixture) | 54 | 1.35 | 150-450 |
| Second particulate agent (popping candy) | 30 | 0.75 | 800-1500 |

| Ingredient | Amount (%) by mass of composition | Mass (g) | Particle size range (μm) |
|---|---|---|---|
| Encapsulated cocodamol (paracetamol, codeine, encapsulant; combined) | 30 | 0.5; 0.008; 0.25; 0.758 | 200-500 |
| First particulate agent (caster sugar and powdered flavouring mixture) | 40 | 0.93 | 150-450 |
| Second particulate agent (popping candy) | 30 | 0.75 | 800-1500 |

| Ingredient | Amount (%) by mass of composition | Mass (g) | Particle size range (μm) |
|---|---|---|---|
| Encapsulated codeine (codeine, encapsulant; combined) | 5 | 0.015; 0.1; 0.115 | 200-500 |
| First particulate agent (caster sugar and powdered flavouring mixture) | 65 | 1.63 | 150-450 |
| Second particulate agent (popping candy) | 30 | 0.75 | 800-1500 |

| Ingredient | Amount (%) by mass of composition | Mass (g) | Particle size range (μm) |
|---|---|---|---|
| Encapsulated Pseudoephedrine Hydrochloride (Pseudoephedrine Hydrochloride, encapsulant; combined) | 6 | 0.06; 0.1; 0.16 | 200-500 |
| First particulate agent (caster sugar and powdered flavouring mixture) | 64 | 1.6 | 150-450 |
| Second particulate agent (popping candy) | 30 | 0.75 | 800-1500 |

| Ingredient | Amount (%) by mass of composition | Mass (g) | Particle size range (μm) |
|---|---|---|---|
| Phenylephrine Hydrochloride | 0.5 | 0.012 | 200-500 |
| First particulate agent (caster sugar and powdered flavouring mixture) | 69.5 | 1.738 | 150-450 |
| Second particulate agent (popping candy) | 130 | 0.75 | 800-1500 |

| Ingredient | Amount (%) by mass of composition | Mass (g) | Particle size range (μm) |
|---|---|---|---|
| Cetirizine Hydrochloride | 0.4 | 0.01 | 200-500 |
| First particulate agent (caster sugar and powdered flavouring mixture) | 69.6 | 1.74 | 150-450 |
| Second particulate agent (popping candy) | 30 | 0.75 | 800-1500 |

| Ingredient | Amount (%) by mass of composition | Mass (g) | Particle size range (μm) |
|---|---|---|---|
| Methylphenidate Hydrochloride | 0.4 | 0.01 | 200-500 |
| First particulate agent (caster sugar and powdered flavouring mixture) | 69.6 | 1.74 | 150-450 |
| Second particulate agent (popping candy) | 30 | 0.75 | 800-1500 |

Variants of the above exemplary compositions further comprising caffeine may also be produced, in particular compositions comprising caffeine and one or more of paracetamol, aspirin and ibuprofen.

Example 9

The second particulate agent may be selected to be an insoluble agent, such as powdered nuts. In such a composition of the invention, the particle size of the second particulate agent is not particularly limited. Thus, the first and second particulate agents may be selected to have similar particle sizes.

| Ingredient | Amount (%) by mass of composition | Mass (g) | Particle size range (μm) |
|---|---|---|---|
| Encapsulated caffeine (caffeine, encapsulant; combined) | 14 | 0.18; 0.18; 0.36 | 200-500 |
| First particulate agent (caster sugar and powdered flavouring mixture) | 20 | 0.5 | 150-450 |
| Second particulate agent (ground almonds) | 66 | 1.64 | 100-200 |

The present disclosure also includes the following:
1. An oral particulate composition comprising:
a poor or bitter tasting agent;
a first particulate agent for facilitating swallowing of the poor or bitter tasting agent to reduce the time of residence in the mouth of the poor or bitter tasting agent; and
a second particulate agent having a larger particle size than the first particulate agent so as to remain in the mouth after the poor or bitter tasting agent has been swallowed to block or mask a bitter aftertaste ordinarily imparted by the poor or bitter tasting agent.
2. The oral particulate composition of item 1, wherein the first particulate agent stimulates saliva production to facilitate swallowing of the poor or bitter tasting agent.
3. The oral particulate composition of item 1 or 2, wherein the first particulate agent has a solubility profile such that it dissolves in saliva to carry the poor or bitter tasting agent out of the mouth.
4. The oral particulate composition of any preceding item, wherein the first particulate agent has a faster rate of dissolution in saliva than that of the poor or bitter tasting agent.
5. The oral particulate composition of any preceding item, wherein the first particulate agent entrains the poor or bitter tasting agent to facilitate swallowing of the poor or bitter tasting agent with the first particulate agent.
6. The oral particulate composition of any preceding item, wherein the first particulate agent comprises one or more sugars.
7. The oral particulate composition of item 6, wherein the one or more sugars are selected from the list comprising sucrose, glucose, fructose, galactose, mannose, ribose, xylose, maltose and lactose.
8. The oral particulate composition of any preceding item, wherein the first particulate agent comprises one or more sweeteners.
9. The oral particulate composition of item 8, wherein the one or more sweeteners are selected from the list comprising stevia, saccharin, aspartame, sucralose, neotame, acesulfame potassium, advantame, sorbitol and xylitol.
10. The oral particulate composition of any preceding item, wherein the first particulate agent comprises one or more flavourings.
11. The oral particulate composition of item 10, wherein the one or more flavourings are selected from the list comprising a mint, menthol, ginger, liquorice, cinnamon, aniseed, fruit, chocolate, coffee, citrus and cola flavouring.
12. The oral particulate composition of any preceding item, wherein the mean particle size of the first particulate agent is in the range 100 μm to 500 μm or more preferably in the range 150 μm to 450 μm.
13. The oral particulate composition of any preceding item, wherein at least 90% of the particles of the first particulate agent have a particle size in the range 100 μm to 500 μm, and more preferably in the range 150 μm to 450 μm.
14. The oral particulate composition of any preceding item, wherein the second particulate agent comprises one or more sugars.
15. The oral particulate composition of item 14, wherein the one or more sugars are selected from the list comprising sucrose, glucose, fructose, galactose, mannose, ribose, xylose, maltose and lactose.
16. The oral particulate composition of any preceding item, wherein the second particulate agent comprises one or more sweeteners.
17. The oral particulate composition of item 16, wherein the one or more sweeteners are selected from the list comprising stevia, saccharin, aspartame, sucralose, neotame, acesulfame potassium, advantame, sorbitol and xylitol.
18. The oral particulate composition of any preceding item, wherein the second particulate agent comprises one or more flavourings.
19. The oral particulate composition of item 18, wherein the one or more flavourings are selected from the list comprising a mint, menthol, ginger, liquorice, cinnamon, aniseed, fruit, chocolate, coffee, citrus and cola flavouring.
20. The oral particulate composition of any preceding item, wherein the second particulate agent comprises particles of one or more of: a dried fruit, a gel, a jelly, a mint sweet, a candy, and a chocolate.
21. The oral particulate composition of any preceding item, wherein the second particulate agent comprises particles of a carbonated candy such as a popping candy.
22. The oral particulate composition of item 21, wherein the particles of a carbonated candy have coatings of at least one of sugar and hard candy.
23. The oral particulate composition of any preceding item, wherein the mean particle size of the first particulate agent is at least 500 μm, and is more preferably at least 800 μm.
24. The oral particulate composition of any preceding item, wherein at least 90% of the particles of the first particulate agent have a particle which is at least 500 µm, and which is more preferably at least 800 µm.

25. The oral particulate composition of any preceding item, wherein the poor or bitter tasting agent comprises one or more bioactive agents selected from the list comprising caffeine, at least one vitamin or mineral or a combination thereof, dextromethorphan, chlorhexidine, guaifenesin, pseudoephedrine, peroxide, statins, acetaminophen, diphenhydramine, doxylamine, sildenafil citrate and loperamide or a combination thereof, and an over-the-counter drug or medicine selected from the list comprising a painkiller and/or an anti-inflammatory such as ibuprofen, paracetamol, aspirin or codeine, an antihistamine, a cold or flu remedy, a health supplement, a nausea remedy, a travel-sickness remedy, a heart burn treatment, an agent to assist digestion.

26. The oral particulate composition of any preceding item, wherein the poor or bitter tasting agent is provided in particulate form, or as a liquid soaked onto a solid carrier.

27. The oral particulate composition of any preceding item, wherein the poor or bitter tasting agent has a mean particle size smaller than the mean particle size of the second particulate agent.

28. The oral particulate composition of any preceding item, wherein the poor or bitter tasting agent has a mean particle size similar to the mean particle size of the first particulate agent.

29. The oral particulate composition of any preceding item, wherein the poor or bitter tasting agent is provided in a powdered form.

30. The oral particulate composition of any preceding item, wherein the poor or bitter tasting agent is provided in an encapsulated form.

31. The oral particulate composition of item 30, wherein the encapsulant comprises at least one of a lipid and a polysaccharide.

32. The oral particulate composition of item 30 or 31, wherein the encapsulant provides 10 to 90% by mass of the encapsulated poor or bitter tasting agent and preferably 45 to 55%.

33. The oral particulate composition of any preceding item, wherein poor or bitter tasting agent has a particle size of 800 µm or less.

34. The oral particulate composition of any preceding item, wherein the poor or bitter tasting agent has a particle size of 200 µm or less.

35. The oral particulate composition of any preceding item, wherein oral particulate composition is a free-flowing particulate composition.

36. The oral particulate composition of any preceding item, wherein the poor or bitter tasting agent consists of particles of encapsulated caffeine.

37. The oral particulate composition of item 36, wherein the weight ratio of the caffeine to the encapsulate is approximately 1:1.

38. The oral particulate composition of item 37, wherein the weight ratio of first particulate agent to the encapsulated caffeine particles is from 1:1 to 3:1, and is preferably 15:4.

39. The oral particulate composition of item 37 or 38, wherein the weight ratio of second particulate agent to first particulate agent is from 1:1 to 1:3, and is preferably 6:15.

40. The oral particulate composition of any of items 37 to 39, wherein the weight ratio of second particulate agent to encapsulated caffeine particles is from 1:1 to 2:1, and is preferably 3:2.

41. An oral dosage form of the oral particulate composition of any of items 1 to 40.

42. The oral dosage form of item 41, wherein when the poor or bitter tasting agent comprises caffeine, in an amount of 200 mg or less of caffeine.

43. The oral dosage form of item 41 or 42, wherein the total mass of the oral dosage form is in the range 0.5 g to 5 g.

44. The oral dosage form of any of items 41 to 43, wherein the total mass of the dosage form is in the range 2.0 g to 3 g.

45. The oral dosage form of any of items 41 to 44, consisting of encapsulated caffeine particles as the poor or bitter tasting agent, a sugar-based first particulate agent and a popping candy as second particulate agent.

46. The oral dosage form of any of items 41 to 44, consisting of encapsulated caffeine particles as the poor or bitter tasting agent, a sugar-based first particulate agent and hard boiled or compressed tab mint second particulate agent.

47. The oral dosage form of any of any of items 41 to 46, consisting of up to 400 mg of encapsulated caffeine particles, 1500 mg of the first particulate agent and 600 mg of the second particulate agent.

48. A packaged dosage form comprising the oral dosage form of any of items 41 to 47 and a packaging material.

49. The packaged dosage form of item 48, wherein the packaging material comprises a sachet.

50. A free-flowing particulate composition suitable for oral consumption, comprising:
    encapsulated caffeine particles, having a particle size of less than 800 µm;
    a sugar-based carrier phase having particles with a particle size in the range 100 µm to 500 µm; and
    a sugar-based retained phase having particles with a particle size of at least 800 µm.

51. The free-flowing particulate composition of item 50, wherein the sugar-based carrier phase comprises at least one sugar selected from the list including sucrose, glucose, fructose, galactose, mannose, ribose, xylose, maltose and lactose.

52. The free-flowing particulate composition of item 50 or 51, wherein the sugar-based retained phase comprises at least one sugar selected from the list including sucrose, glucose, fructose, galactose, mannose, ribose, xylose, maltose and lactose.

53. The free-flowing particulate composition of any of items 50 to 52, wherein the mean particle size of the encapsulated caffeine particles is less than 500 µm, and more preferably less than 200 µm.

54. The free-flowing particulate composition of any of items 50 to 53, wherein the size of the sugar-based carrier phase particles is preferably in the range 150 µm to 450 µm.

55. The free-flowing particulate composition of any of items 50 to 54, wherein the size of the sugar-based retained phase particles is preferably in the range 800 µm to 1500 µm.

56. The free-flowing particulate composition of any of items 50 to 55, wherein the weight ratio of sugar-based carrier phase to encapsulated caffeine particles is from 1:1 to 3:1, and is preferably 15:4.

57. The free-flowing particulate composition of any of items 50 to 56, wherein the weight ratio of sugar-based retained phase to sugar-based carrier phase is from 1:1 to 1:3, and is preferably 6:15.

58. The free-flowing particulate composition of any of items 50 to 57, wherein the weight ratio of sugar-based retained phase to encapsulated caffeine particles is from 1:1 to 2:1, and is preferably 3:2.

59. The free-flowing particulate composition of any of items 50 to 58, wherein the sugar-based retained phase comprises particles of at least one of a dried fruit, a gel, a jelly, a mint sweet, and a candy.

60. The oral particulate composition of any of items 50 to 59, wherein the second particulate agent comprises particles of a carbonated candy such as a popping candy.

61. The oral particulate composition of item 60, wherein the particles of a carbonated candy have coatings of at least one of sugar and hard candy.

62. The free-flowing particulate composition of any of items 50 to 61, wherein the particles of at least one of the carrier phase and the retained phase are flavoured with at least one of a mint, menthol, ginger, liquorice, cinnamon, aniseed, fruit, chocolate, coffee, citrus and cola flavouring.

63. The free-flowing particulate composition of any of items 50 to 62, wherein the encapsulated caffeine particles comprise caffeine and a lipid or polysaccharide coating.

64. The free-flowing particulate composition of item 63, the caffeine provides 40 to 60% by mass of the encapsulated caffeine particles and preferably 45 to 55%.

65. An oral dosage form of the free-flowing particulate composition of any of items 50 to 64.

66. The oral dosage form of item 65, comprising 200 mg or less of caffeine.

67. The oral dosage form of item 65 or 66, wherein the total mass of the dosage form is in the range 0.5 g to 5 g.

68. The oral dosage form of any of items 65 to 67, wherein the total mass of the dosage form is in the range 2.5 g to 3 g.

69. The oral dosage form of item 65 or 68, consisting of 400 mg of encapsulated caffeine particles, 1500 mg of the sugar-based carrier phase and 600 mg of the sugar-based retained phase.

70. A packaged dosage form comprising the oral dosage form of any of items 65 to 69 and a packaging material.

71. The packaged dosage form of item 70, wherein the packaging material comprises a sachet.

The invention claimed is:

1. A free-flowing particulate composition suitable for oral consumption, comprising:
   a carrier phase which is a free-flowing particulate phase comprising (a) a bitter tasting agent having a mean particle size, inclusive of any encapsulant, coating or other substrate, of less than 500 μm, and (b) a first particulate agent which is sugar particles having a mean particle size of 100-500 μm; and
   a retained phase which is a free-flowing particulate phase, comprising a second particulate agent, wherein the second particulate agent comprises particles comprising a sugar having a mean particle size of at least 800 μm, and wherein the second particulate agent is other than chewing gum; and
   wherein the particles of the retained phase are able to move freely with respect to the particles of the carrier phase, the size of particles of the second particulate agent are larger than those of the first particulate agent, and D75 of the second particulate agent is greater than D75 of the first particulate agent.

2. The particulate composition according to claim 1, wherein a residence time in the mouth of the retained phase ($R_{90}$: retained) is at least 10 seconds.

3. The particulate composition according to claim 1, wherein the second particulate agent has a dissolution rate in water of at least 15 seconds, wherein the dissolution rate is determined as the time taken for 50% by mass of the material to dissolve, following addition of 1 g of material to 10 mL stirred water at 37° C.

4. The particulate composition according to claim 1, wherein the retained phase is the second particulate agent and wherein the second particulate agent is selected from:
   (a) particles of sugar;
   (b) compressed powdered sweets;
   (c) hard candy; or
   (d) popping candy; and
   wherein the particles of sugar, compressed powdered sweets, hard candy and popping candy may optionally comprise one or more flavouring and/or colouring agents and comprise at least 90 wt. % sugar.

5. The particulate composition according to claim 1, wherein the second particulate agent comprises at least 90 wt. % sugar.

6. The particulate composition according to claim 1 wherein the second particulate agent comprises particles of popping candy.

7. The particulate composition according to claim 6, wherein the particles of popping candy have coatings of at least one of sugar and hard candy.

8. The particulate composition according to claim 1, wherein the second particulate agent comprises added flavouring.

9. The particulate composition according to claim 1, wherein the bitter tasting agent comprises caffeine.

10. The particulate composition according to claim 1, wherein the bitter tasting agent comprises a medicament.

11. The particulate composition according to claim 1, wherein the bitter tasting agent comprises at least one of:
   (a) one or more medicaments selected from aspirin, paracetamol, ibuprofen, cocodamol and codeine, or a pharmaceutically acceptable salt thereof, each of which may optionally be present in combination with caffeine and/or phenylephrine or a pharmaceutically acceptable salt thereof;
   (b) one or more antihistamines; or
   (c) one or more medicaments selected from methylphenidate, amphetamine, dextroamphetamine, amphetamine/dextroamphetamine, dexmethylphenidate, lisdexamfetamine, amitriptyline, desipramine, imipramine, nortriptyline, bupropion, citalopram, escitalopram, sertraline and venlafaxine, or a pharmaceutically acceptable salt thereof.

12. The particulate composition according to claim 1, wherein the bitter tasting agent is encapsulated.

13. The particulate composition according to claim 12, wherein the bitter tasting agent is encapsulated caffeine particles, and the encapsulated caffeine particles comprise caffeine and a lipid or polysaccharide coating.

14. The particulate composition according to claim 13, wherein the caffeine provides 40 to 60% by mass of the encapsulated caffeine particles.

15. The particulate composition according to claim 1, wherein the first particulate agent has a mean particle size in the range of 150 μm to 450 μm.

16. The particulate composition according to claim 1, wherein the second particulate agent comprises at least 90 wt. % sugar and has a mean particle size in the range of 800 μm to 1500 μm.

17. The particulate composition according to claim 1, wherein the mean particle size of the bitter tasting agent, inclusive of any encapsulant, coating or other substrate, is less than 200 μm.

18. The particulate composition according to claim 17, wherein a weight ratio of the sugar particles of the first particulate agent to encapsulated caffeine particles is from 1:1 to 3:1.

19. The particulate composition according to claim 18, wherein a weight ratio of the sugar particles of the second particulate agent to the sugar particles of the first particulate agent is from 1:1 to 1:3.

20. The particulate composition according to claim 1, wherein the sugar particles of the first particulate agent comprise one or more flavouring and/or colouring agents.

21. A free-flowing particulate composition suitable for oral consumption, comprising:
- a carrier phase which is a free-flowing particulate phase, wherein the carrier phase comprises encapsulated caffeine particles, having a mean particle size of less than 800 μm, and a sugar-based carrier component having particles with a mean particle size in the range of 100 μm to 500 μm; and
- a retained phase comprising a sugar-based retained component having particles with a mean particle size of at least 800 μm, wherein D75 of the retained phase is greater than D75 of the sugar-based carrier component.

22. An oral dosage form of the particulate composition of claim 1.

23. The oral dosage form according to claim 22, comprising 200 mg or less of caffeine.

24. The oral dosage form according to claim 22, wherein the total mass of the dosage form is in the range 0.5 g to 5 g.

25. The oral dosage form according to claim 22, consisting of:
- 400 mg±40 mg of encapsulated caffeine particles;
- 1500 mg±150 mg of the first particulate agent; and
- 600 mg±60 mg of the second particulate agent.

26. A packaged dosage form comprising the oral dosage form of claim 22 and a packaging material.

27. The particulate composition according to claim 1, wherein the second particulate agent is flavoured popping candy.

* * * * *